(12) United States Patent
Fitzgerald et al.

(10) Patent No.: US 10,406,341 B2
(45) Date of Patent: Sep. 10, 2019

(54) CONNECTOR FOR CONNECTING A SYRINGE TO A GASTRONOMY TUBE

(75) Inventors: Alan Fitzgerald, Edgeworthstown (IE); Ciara Deighan, Birr (IE); Paul J. Daly, Tullamore (IE)

(73) Assignee: KPR U.S., LLC, Mansfield, MA (US)

( * ) Notice: Subject to any disclaimer, the term of this patent is extended or adjusted under 35 U.S.C. 154(b) by 1221 days.

(21) Appl. No.: 14/003,654

(22) PCT Filed: Mar. 7, 2012

(86) PCT No.: PCT/US2012/028061
§ 371 (c)(1),
(2), (4) Date: Oct. 21, 2014

(87) PCT Pub. No.: WO2012/122261
PCT Pub. Date: Sep. 13, 2012

(65) Prior Publication Data
US 2018/0177993 A1    Jun. 28, 2018

(30) Foreign Application Priority Data
Mar. 9, 2011 (EP) .................................. 11001934

(51) Int. Cl.
*A61M 39/10* (2006.01)
*A61J 15/00* (2006.01)
*A61M 39/20* (2006.01)

(52) U.S. Cl.
CPC ...... *A61M 39/1011* (2013.01); *A61J 15/0026* (2013.01); *A61J 15/0015* (2013.01);
(Continued)

(58) Field of Classification Search
CPC .............. A61M 39/1011; A61M 39/20; A61M 2039/1033; A61M 2039/1077; A61M 25/0014; A61J 15/0026
See application file for complete search history.

(56) References Cited

U.S. PATENT DOCUMENTS

| | | | | |
|---|---|---|---|---|
| 4,511,359 A | * | 4/1985 | Vaillancourt | ......... A61M 39/14 285/3 |
| 4,950,254 A | * | 8/1990 | Andersen | ............ A61J 15/0026 604/213 |

(Continued)

FOREIGN PATENT DOCUMENTS

| | | | | |
|---|---|---|---|---|
| JP | 2549223 B2 | * | 10/1996 | .......... A61M 39/045 |
| JP | 2549223 B2 | | 10/1996 | |

(Continued)

OTHER PUBLICATIONS

Japanese Office Action dated Jul. 31, 2014 in related Patent Application JP2013-557829, 9 pages.
(Continued)

*Primary Examiner* — Jenna Zhang (57) ABSTRACT

A connector (10) for connecting a syringe to a gastrostomy tube (12), the connector (10) comprises a bayonet style locking member (16) with a locking projection (40) for locking the connector (10) to the gastrostomy tube (12). The locking projection (40) forms a receiving recess (42) for receiving and locking at least one wing (70) of an end portion (56) of the gastrostomy tube (12). Further, the invention relates to a connector assembly having such a connector (10) and to a method for connecting a syringe to a gastrostomy tube (12).

20 Claims, 9 Drawing Sheets

(52) U.S. Cl.
CPC ........... *A61J 15/0076* (2015.05); *A61M 39/20* (2013.01); *A61M 2039/1077* (2013.01)

(56) References Cited

U.S. PATENT DOCUMENTS

| | | | | |
|---|---|---|---|---|
| 5,057,093 | A | * | 10/1991 | Clegg ................... A61M 39/10 128/912 |
| 5,201,717 | A | * | 4/1993 | Wyatt ................... A61M 39/04 128/912 |
| 5,267,938 | A | * | 12/1993 | Konotchick ............. A61N 2/02 600/9 |
| 5,267,983 | A | * | 12/1993 | Oilschlager ......... A61J 15/0026 285/148.24 |
| 5,569,222 | A | * | 10/1996 | Haselhorst ............ A61M 39/10 604/533 |
| 5,658,260 | A | * | 8/1997 | Desecki ................ A61J 1/2089 604/239 |
| 5,776,117 | A | * | 7/1998 | Haselhorst ............ A61M 39/10 604/533 |
| 2003/0216712 | A1 | * | 11/2003 | Kessler ............... A61J 15/0015 604/533 |
| 2003/0216713 | A1 | * | 11/2003 | Kessler ............... A61J 15/0015 604/533 |
| 2006/0004345 | A1 | * | 1/2006 | McMichael ........... A61M 39/10 604/523 |
| 2006/0149211 | A1 | * | 7/2006 | Simpson ........... A61M 5/16804 604/403 |
| 2007/0083262 | A1 | * | 4/2007 | Matlock ........... A61M 16/0465 623/9 |
| 2010/0036365 | A1 | * | 2/2010 | Becker ................ A61M 39/10 604/533 |

FOREIGN PATENT DOCUMENTS

| | | | | |
|---|---|---|---|---|
| JP | 2010507419 | A | * 3/2010 | ........... A61M 39/10 |
| JP | 2010507419 | A | 3/2010 | |
| JP | 2010-179180 | A | 8/2010 | |
| WO | 91/07206 | | 5/1991 | |

OTHER PUBLICATIONS

European Search Report for EP 11 001 934 dated Aug. 18, 2011, 8 pages.
International Search Report regarding corresponding PCT/US2012/028061, dated Sep. 28, 2012, 5 pages.
Written Opinion of the International Searching Authority, PCT/US2012/028061, dated Sep. 28, 2012, 5 pages.

* cited by examiner

CONNECTOR FOR CONNECTING A SYRINGE TO A GASTRONOMY TUBE

BACKGROUND OF INVENTION

Field of the Invention

The invention relates to a connector for connecting a syringe to a gastrostomy tube.

The connector of the present invention in particular is used in the field of medical supplies and nursing care.

Related Art

Connectors for connecting medical tubes to other medical devices are known in the art.

U.S. Pat. No. 4,511,359 describes a sterile connection device having a protector which may be pierced, penetrated or opened by pressurized fluid flow, wherein the protector is closed to the passage of unwanted contaminants.

U.S. Pat. No. 5,057,093 discloses a medical device for use between a feeding tube set and a catheter with an universal adaptor for permitting the use of the medical device with connectors of various sizes.

U.S. Pat. No. 5,267,983 describes a multistepped adaptor, the steps becoming smaller in a longitudinal direction for accommodating a wide range of diameters or access ports of enteral feeding devices.

U.S. Pat. No. 5,569,222 discloses a stepped adaptor wherein the diameter of the sections at the exterior of the body of the adaptor increasing from the one end of the adaptor to the other end of the adaptor. Thus, the adaptor can be connected to a variety of tubes having variously sized access ports.

U.S. Pat. No. 5,201,717 describes a connector to connect a gastrostomy tube to a syringe comprising bayonet style locking projections being arranged in parallel to the surface of a needle extending between two locking projections.

US 2006/0149211 A1 discloses a connector to connect two medical accessories, the connector comprising two bayonet style locking members, wherein a valve is extending between the two locking members.

US 2010/0036365 A1 describes a connector to connect a feeding probe to a transfer system, the connector comprising a bayonet style groove, wherein an insertion tube extends parallel to the extending direction of the bayonet style groove.

When initially inserting a gastrostomy tube, a surgeon creates a stoma, which is an opening in the patient's body extending through the abdominal and stomach walls. The gastrostomy tube is inserted into the stoma to allow food (Nutritional Formula) to be delivered directly to the stomach. A connector can be used in conjunction with the gastrostomy tube to allow syringes supplying medication or supplements to be attached to the tube. These connectors should be closely and securely attached to the gastrostomy tube in order to avoid that the connector detaches from the gastrostomy tube.

SUMMARY

One or more aspects of the present invention provide a connector and a method for connecting enteral feeding sets and syringes to a gastrostomy tube in a close and secure manner.

The connector can comprise a bayonet style locking member with a locking projection for locking the connector to a gastrostomy tube, wherein the locking projection forms a receiving recess for receiving and locking at least one wing of an end portion of the gastrostomy tube.

An end portion of the gastrostomy tube thus can be received in the receiving recess and locked therein such that a close and secure connection between the connector and the gastrostomy tube can be attained.

A bayonet style locking member can comprise at least one locking projection and/or at least one receiving recess.

The bayonet style locking member can comprise a body portion with a connecting surface and with a through hole extending in a longitudinal direction.

All nourishment, medication or medical supplements can be inserted at one end of the through hole and thus applied to the patient.

The locking projection can comprise a connecting portion extending substantially in the longitudinal direction and a free end portion extending substantially perpendicular to the connecting portion towards an insertion tube configured to be received in the gastrostomy tube. The receiving recess is preferably formed by the connecting portion, the free end portion and/or the connecting surface. Preferably, the connecting portion, the free end portion and/or the receiving portion can be shaped substantially rectangular. Thus, the end portion of the gastrostomy tube can be easily inserted into the receiving recess without the need to change the moving direction at insertion of the end portion.

Preferably, the receiving recess extends linear or arc-shaped substantially perpendicular to the longitudinal direction. Such an extension provides a large engagement area between the receiving recess and the end portion. Thus, the connection is more secure than if only a narrow receiving recess is formed to receive the end portion of the gastrostomy tube. Preferably, the receiving recess is shaped substantially rectangular.

In an advantageous embodiment the locking projection is integrally formed with or bonded to the body portion at the connecting surface. A tight fixation of the locking projection to the body portion of the connector as can be realized by bonding or integrally forming provides a protection against breaking of the locking projection for example during handling by a nurse.

The free end portion preferably comprises edges being inclined for narrowing the edges to the receiving recess. The insertion of the end portion into the receiving recess can be eased if the edges of the receiving recess are inclined. The end portion can easily slide into the receiving recess instead of first striking the edge and then clicking into the receiving recess. Thus jerky movements can be avoided which can be painful for the patient.

In a further preferred embodiment at least two locking projections are provided, wherein the free end portions pointing towards each other and being distanced to define an orifice in between. Two or more locking projections provide a more secure connection between the gastrostomy tube and the connector. Advantageously the locking projections can be located symmetrically around the body portion of the connector with an orifice in between such that the end portion of the gastrostomy tube can be passed through the orifice until it is in close contact with the connecting surface of the body portion of the connector.

According to a preferred embodiment an insertion tube is configured to be received in the gastrostomy tube. A combination of the locking projection and an insertion tube provides a more secure connection between the gastrostomy tube and the connector, as the gastrostomy tube is not only held by the locking projection, but also by an engagement with the insertion tube.

Preferably, the insertion tube is attached at the connecting surface and extends substantially in the longitudinal direction. With such an arrangement the gastrostomy tube can be pushed until it contacts the connecting surface of the connector such that the connection can be attained at the outermost point of the gastrostomy tube. Dead space can thus be avoided and the overall assembly can be manufactured as small as possible. This also reduces the lever action by the connector assembly and avoids unnecessary movements of the connector assembly which can be painful for the patient.

It is possible that the insertion tube only extends by a short distance from the connecting surface, or extends to the free end portions of the locking projections, but preferably the insertion tube extends through the orifice over the free end portions of the locking projections. The longer the insertion tube, the more secure is the engagement connection between the gastrostomy tube and the connector. Thus, it may be advantageous if the insertion tube is long and extends through the orifice.

In an advantageous embodiment a passing recess is provided between each free end portion and the insertion tube. Thus, the end portion of the gastrostomy tube can easily be slipped over the insertion tube until it contacts the connecting surface and then be turned such that the end portion is received in the receiving recess. More preferably, the passing recess substantially corresponds to a wall thickness of the gastrostomy tube for fit-passing the gastrostomy tube. Thus, after inserting the insertion tube into the gastrostomy tube and receiving of the end portion by the receiving recess, the gastrostomy tube can be squeezed between the free end portions of the locking projection and the insertion tube. This squeezing can contribute to the close and secure connection between the gastrostomy tube and the connector.

In a further preferred embodiment the insertion tube comprises a plurality of tube portions. Each tube portion is tapered at an outer surface in the longitudinal direction for forming a plurality of abutments. Preferably, the tube portions can be equally formed having an equal diameter. The abutments make the overall diameter of the insertion tube at the outer surface broader and result in a tighter engagement of the gastrostomy tube and the insertion tube. As the insertion tube can comprise several tube portions which are tapered the lower end being inserted first into the gastrostomy tube is smaller in diameter than the abutments and the insertion tube can easily be inserted into the gastrostomy tube. The gastrostomy tube is slipped further upwardly into the direction of the connecting surface. After a short distance it engages the first abutment such that due to the engagement between the abutment and the gastronomy tube a close connection is attained between the two elements. By slipping the gastrostomy tube further upward, the connection becomes more and more tight as more abutments are inserted into the gastrostomy tube. At the end of the slippage a secure connection between the gastrostomy tube and the connector is attained even without inserting the end portion of the gastrostomy tube into the receiving recess.

In an advantageous embodiment the connector comprises a first connector portion with the bayonet style locking member and a second connector portion comprising a syringe attachment member for attaching the syringe. The second connector portion being substantially Y-shaped or T-shaped with a first arm comprising the syringe attachment member and a second arm comprising a feeding attachment member for attaching a feeding tube or container.

Thus, the connection of the gastrostomy tube and the syringe is located at opposite portions of the connector and due to the second connector portion being formed as a Y or T, nourishment as well as medication or supplements can be both dispensed to the patient via the through hole of the connector.

Preferably, the syringe attachment member is formed to receive a syringe in a luer-slip and/or catheter-slip manner.

The syringe attachment member as well as the feeding attachment member can be closed by caps to avoid unwanted contaminants entering the stoma.

A connector assembly comprises a connector as described above and an end portion of a gastrostomy tube being integrally formed with the gastrostomy tube or being formed as adaptor, wherein the end portion comprises at least one wing configured to be received in the receiving recess.

The same applies for a plurality of wings and/or receiving recesses.

Preferably, there are two conditions or positions of the connector assembly as follows: In a first condition of the connector assembly the wing of the end portion does not engage with the receiving recess. In a second condition of the connector assembly the wing of the end portion engages with the receiving recess. In order to bring the connector assembly from the first condition into the second condition the connector is turned, preferably around an axis extending substantially perpendicular to the extension plane of the receiving recess.

In a preferred embodiment a secured locking of the gastrostomy tube and the connector is therefore achieved by a combination of the tapered insertion tube being inserted into the gastrostomy tube and the wings of the end portion of the gastrostomy tube being inserted in the receiving recess or recesses of the bayonet style locking member.

Other aspects pertain to a method for connecting a syringe to a gastrostomy tube comprise the steps of providing a connector according to any of the exemplarily herein disclosed embodiments; providing a gastrostomy tube with an end portion having at least one wing to be connected with the connector, the end portion being integrally formed with the gastrostomy tube or being formed as adaptor; slipping the gastrostomy tube over an insertion tube of the connector; turning the connector to engage the wing of the end portion with the receiving recess; attaching the syringe at the syringe attachment member.

Using this method the gastrostomy tube is preferably slipped over the tapered insertion tube and thus already held after a short distance by the first abutment which is located at the outer surface of the insertion tube. By slipping the gastrostomy further into the direction of the connecting surface, a plurality of abutments engage with the gastrostomy tube making the engagement more secure and tighter. After reaching the connecting surface, the end portion of the gastrostomy tube is inserted into the receiving recess of the connector such that the gastrostomy tube is held to the connector by two forces: first the engagement forces between the abutment of the insertion tube and the gastrostomy tube and second by the retaining forces between the receiving recess and the end portion of the gastrostomy tube. After securely and closely connecting the connector to the gastrostomy tube a syringe can be attached at the opposite end in a common manner, e.g., via a luer-lock, luer-slip or catheter-slip connection, and the medication or supplements can easily be dispensed to the patient. The end portion of the gastrostomy tube can be integrally formed with the gastrostomy tube or can be an adaptor which is subsequently mounted at one end of a common gastrostomy tube to connect it with the described connector.

BRIEF DESCRIPTION OF THE DRAWINGS

The invention will be explained in the following with reference to the drawings in more detail, wherein.

DETAILED DESCRIPTION

Figure 1:
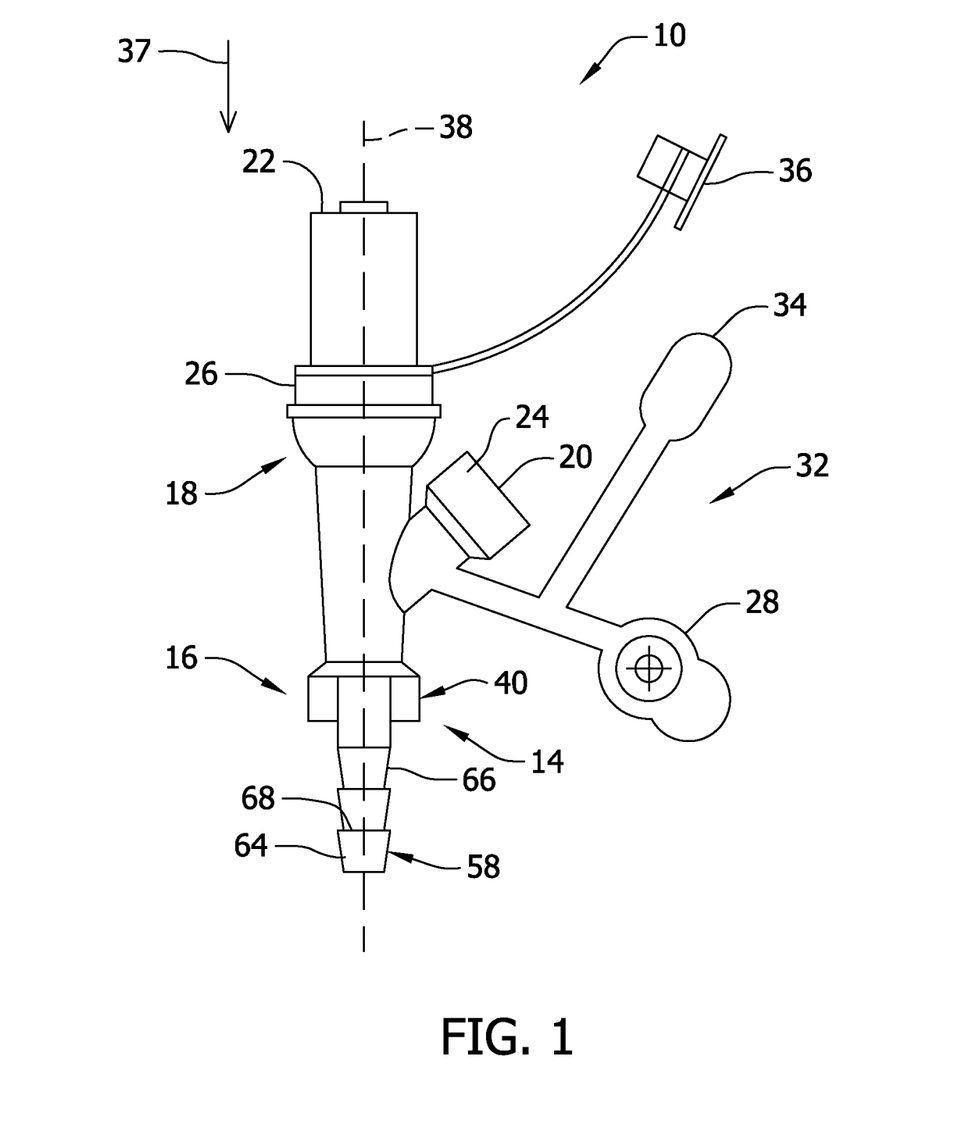
FIG. 1 is a front view showing a first embodiment of a connector.

FIG. 1 shows a first embodiment of a connector 10 for connecting a female luer lock and/or syringes (not shown) to a gastrostomy tube 12 (not shown). The connector 10 comprises a first connector portion 14 with a bayonet style locking member 16 and a second connector portion 18 with a syringe attachment member 20 and a feeding attachment member 22. As the second connector portion 18 is formed Y-shaped, there is a first arm 24 comprising the syringe attachment member 20 and a second arm 26 comprising the feeding attachment member 22.

The syringe attachment member 20 is formed to receive a catheter-slip syringe (not shown). An adaptor 28 for an oral syringe and an adaptor cap 34 are attached to the first arm 24 via a Y-bridge 32. The Y-bridge 32 is preferably made from rubber material such that the Y-bridge 32 can be bent towards the syringe attachment member 20. Thus, the adaptor 28 can be placed in the syringe attachment member 20, and an oral syringe (not shown) can be placed into the adaptor 28. In the case no syringe is placed at the syringe attachment member 20, the adaptor 28 can be closed by an adaptor cap 34.

The feeding attachment member 22 is formed to be connected to a feeding container or tube (not shown). The feeding attachment member 22 can be closed by a feeding cap 36 being attached to the second connector portion 18.

In a longitudinal direction 37 of the connector 10 the word "enteral" is written to avoid confusion with other connectors, e.g., tracheal or gastral connectors.

Figure 2:
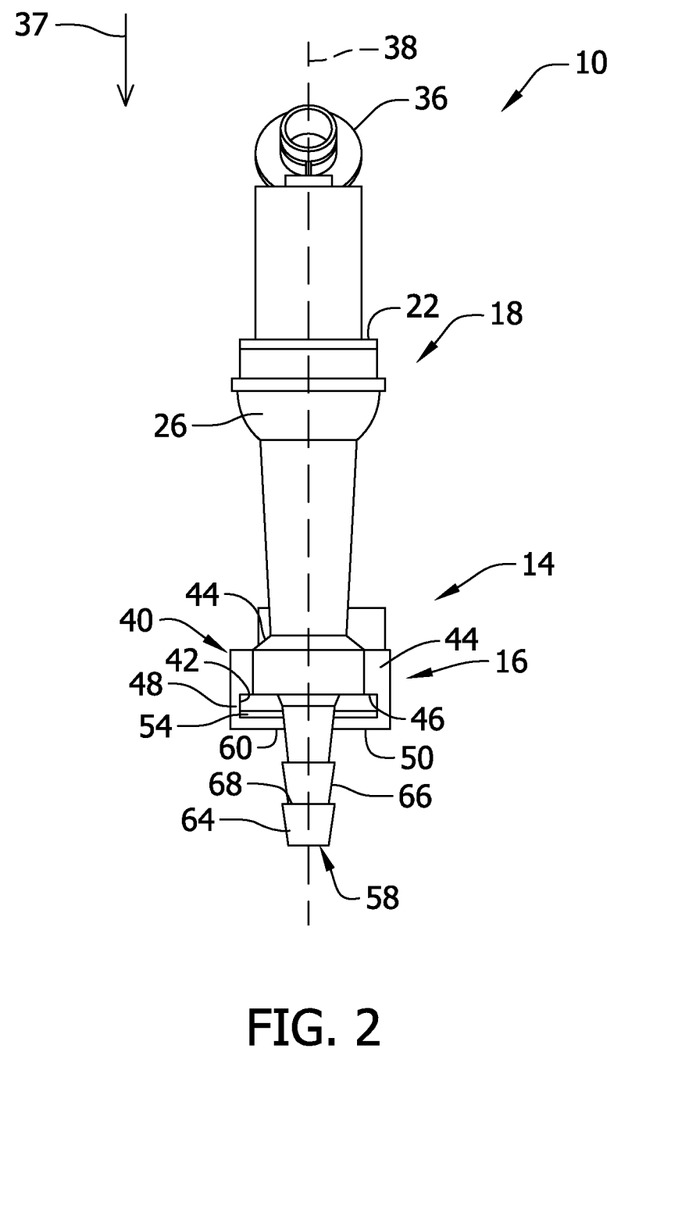
FIG. 2 is a front view of the connector of FIG. 1 turned by 90° around the longitudinal axis.

FIG. 2 shows a front view of the connector 10 of FIG. 1 turned by 90° around a longitudinal axis 38 of the connector 10.

The bayonet style locking member 16 is disposed at the first connector portion 14. The bayonet style locking member 16 may comprise at least one locking projection 40 forming a receiving recess 42. The bayonet style locking member 16 in the shown embodiment comprises two locking projections 40 forming two receiving recesses 42. Further, the bayonet style locking member 16 comprises a body portion 44 and a connecting surface 46. The locking projections 40 are integrally formed or bonded to the body portion 44 and comprise a connecting portion 48 and a free end portion 50. In one embodiment, the locking projections are bonded to the body portion 44. The receiving recess 42 is formed between the connecting surface 46, the connecting portion 48 and the free end portion 50 and is substantially rectangular-shaped, although other shapes are contemplated to accommodate the presence of more than two locking projections 40. A through hole (not shown), through which the nourishment and medication or supplements can be directed into the gastrostomy tube to be dispensed to the patient, is formed in the body portion 44. The through hole extends in the longitudinal direction 37.

The free end portions 50 comprise inclined edges 54 at the side of the receiving recess 42 to make the insertion of an end portion 56 of the gastrostomy tube 12 easier. The free end portions 50 of the two locking projections 40 are pointing to each other. Attached to the connecting surface 46 is an insertion tube 58 which extends in the longitudinal direction 37 through an orifice 60 which is defined between the two free end portions 50.

Figure 3:
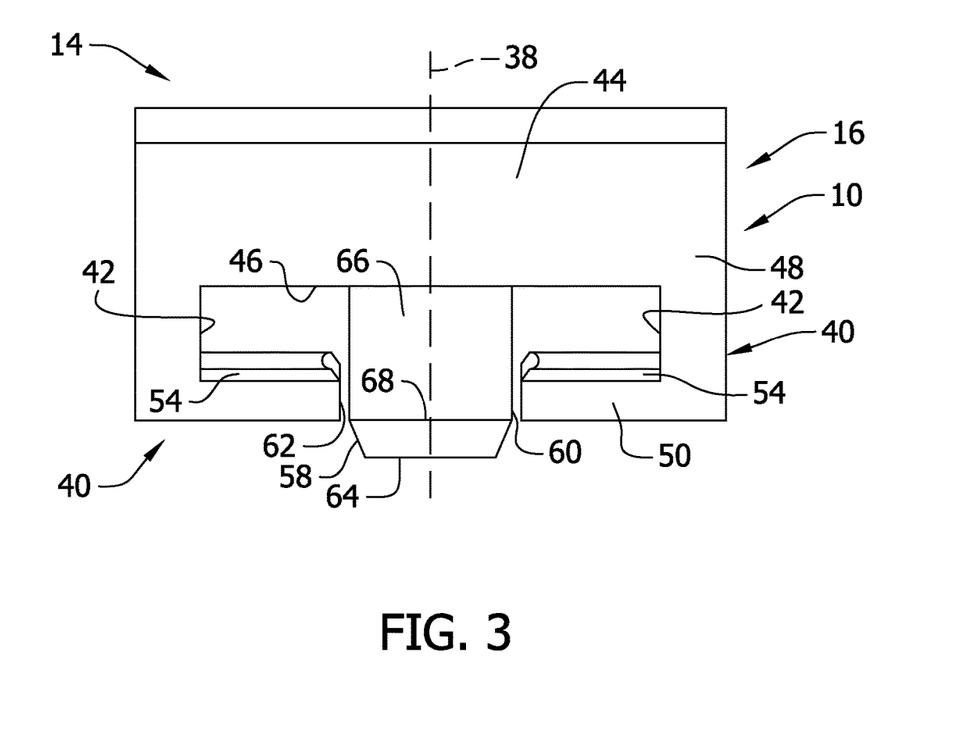
FIG. 3 is an enlarged partial view of the connector shown in FIG. 2.

FIG. 3 shows an enlarged view of the bayonet style locking member 16 with the locking projections 40 and the tube portion 58.

Figure 4:
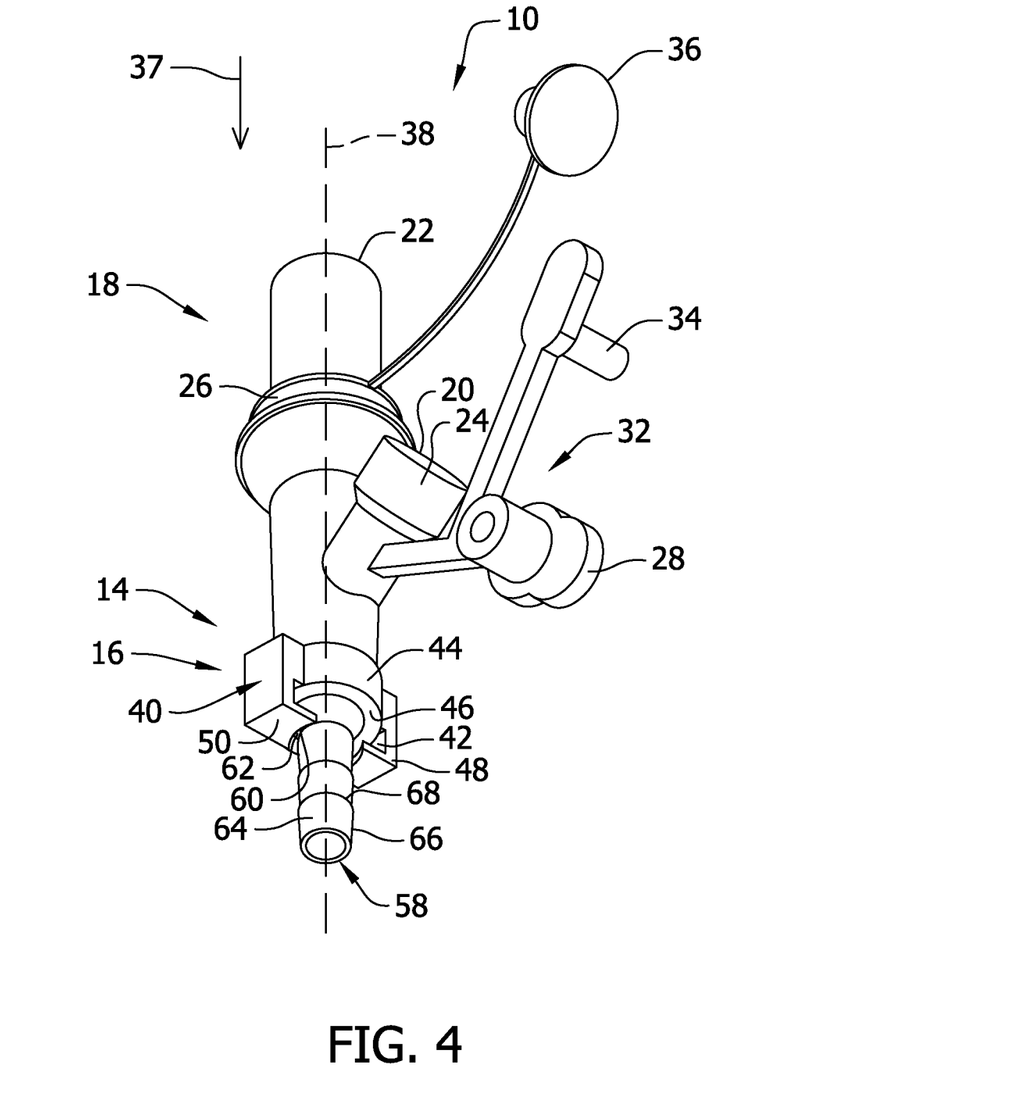
FIG. 4 is a bottom-up perspective view of the connector of FIG. 1.

In FIG. 4 a bottom-up perspective view reveals that between the insertion tube 58 extending through the orifice 60 and the free end portions 50 passing recesses 62 are formed. Thus, the gastrostomy tube 12 can be passed until the end portion 56 contacts the connecting surface 46.

The insertion tube 58 comprises a plurality of tube portions 64 which are tapered at an outer surface 66 in the longitudinal direction 37 such that a plurality of abutments 68 are formed.

Figure 5:
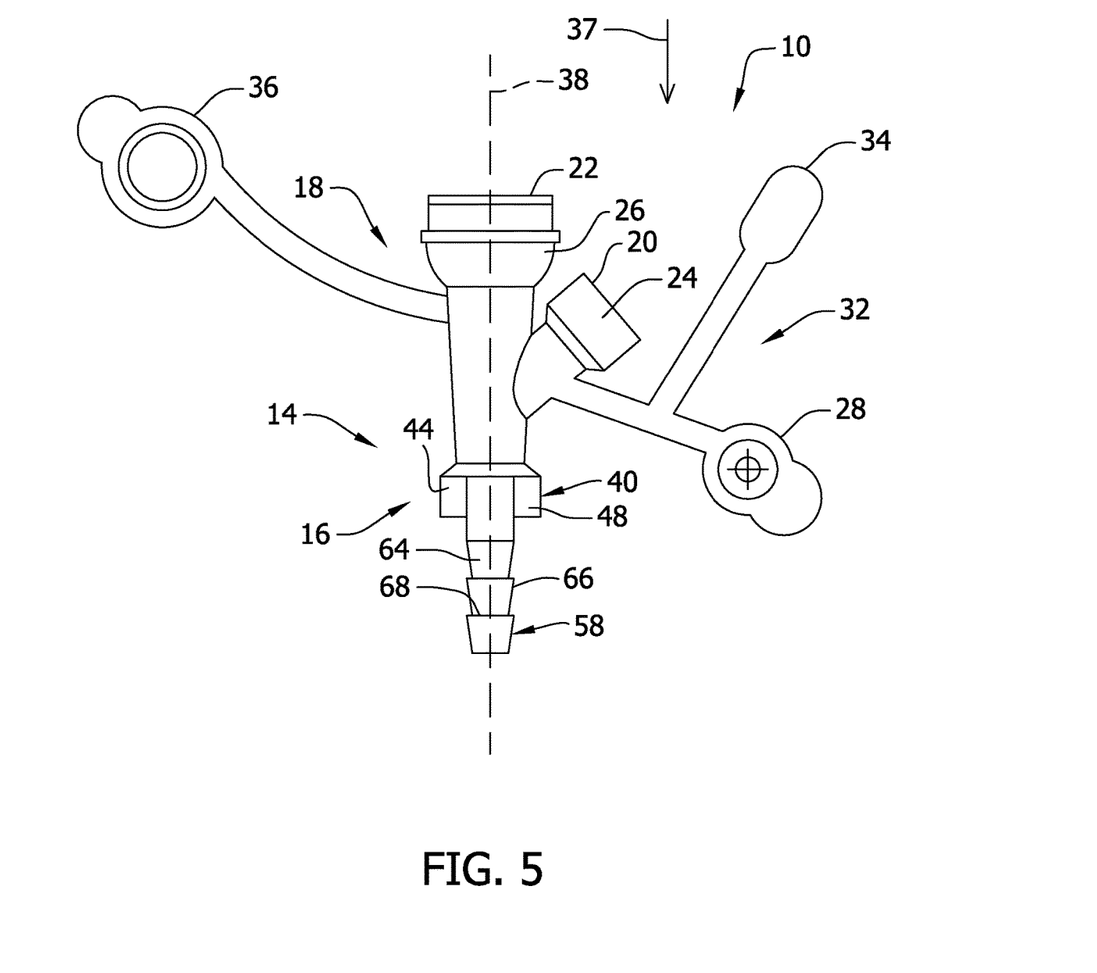
FIG. 5 is a front view of a second embodiment of the connector.
Figure 6:
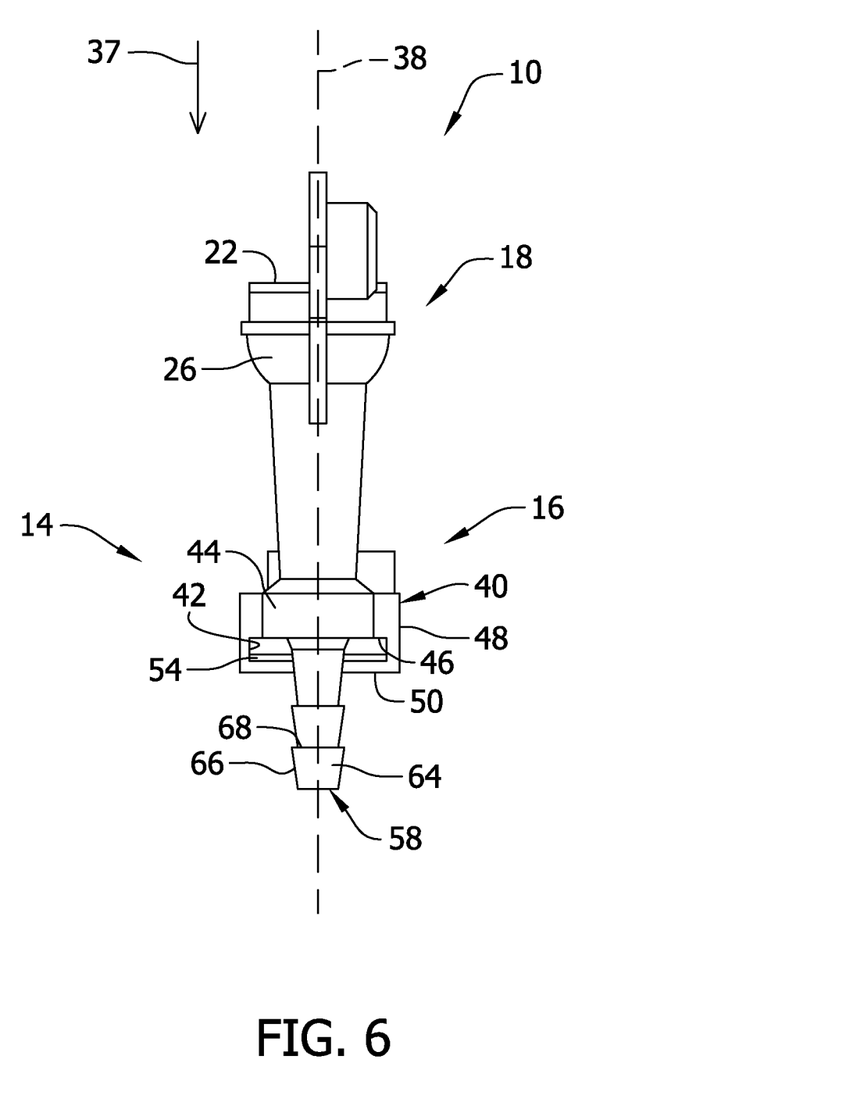
FIG. 6 is a front view of the connector of FIG. 5 turned by 90° along the longitudinal direction.
Figure 7:
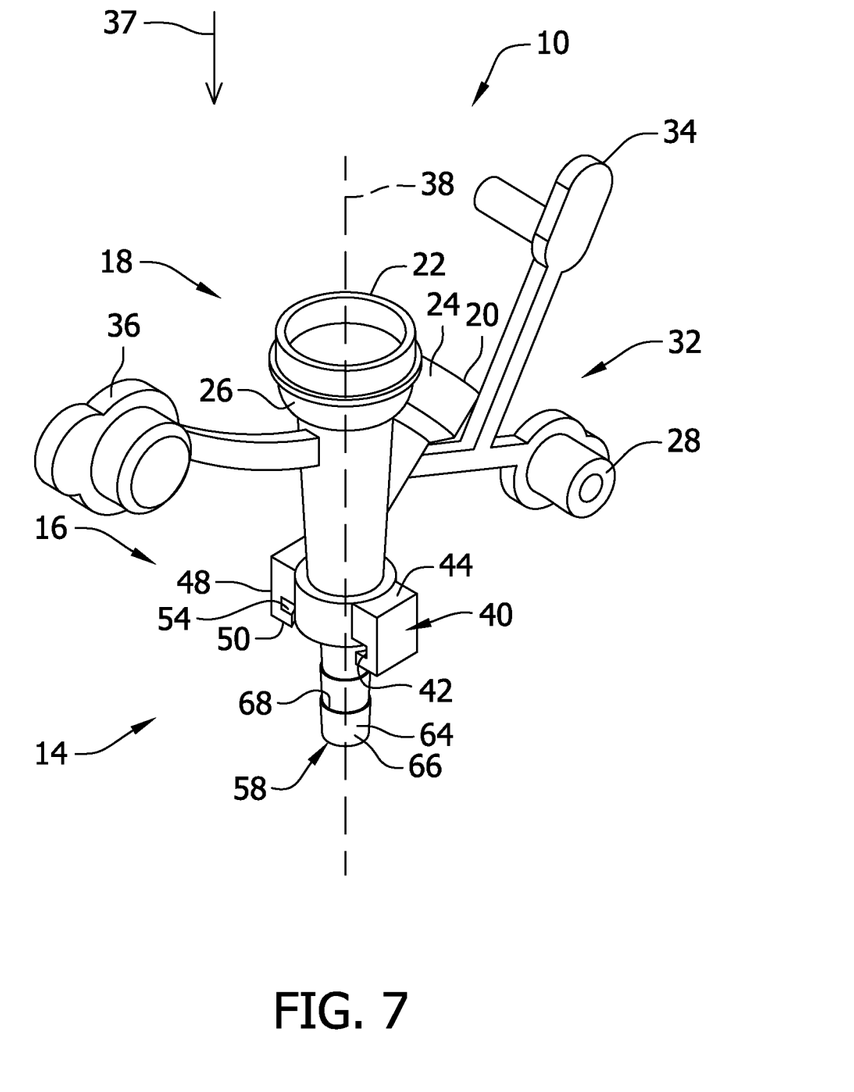
FIG. 7 is a top-down perspective view of the connector of FIG. 5 from above.

FIGS. 5 to 7 show a second embodiment of the connector 10. The connectors 10 of FIGS. 1 to 4 and FIGS. 5 to 7 are basically the same. Thus, same elements are labelled with the same reference signs and are not described in the following for the sake of brevity. There are two differences between the first and second embodiment of connector 10. The first difference is that in FIG. 1 the connector 10 has a feeding attachment member 22 for receiving a feeding tube (not shown) in a luer-lock manner, while in FIG. 5 the feeding attachment member 22 is formed to receive a feeding tube (not shown) in luer-slip or catheter-slip manner. The second difference is that the feeding cap 36 is not attached to the feeding attachment member 22 but to the connector 10.

Figure 8:
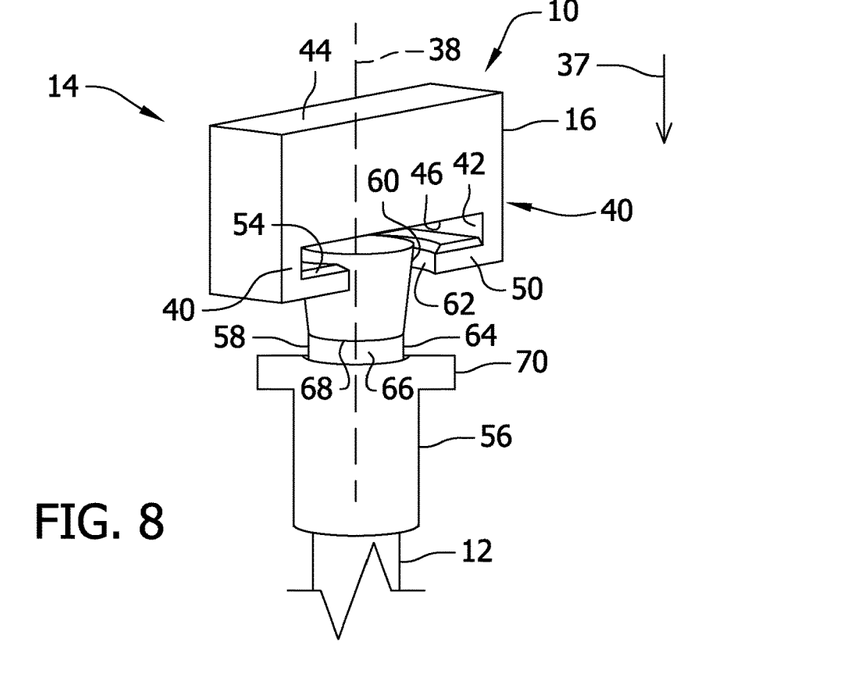
FIG. 8 is a partial view of the connector of FIG. 1 being partially inserted into a gastrostomy tube.
Figure 9:
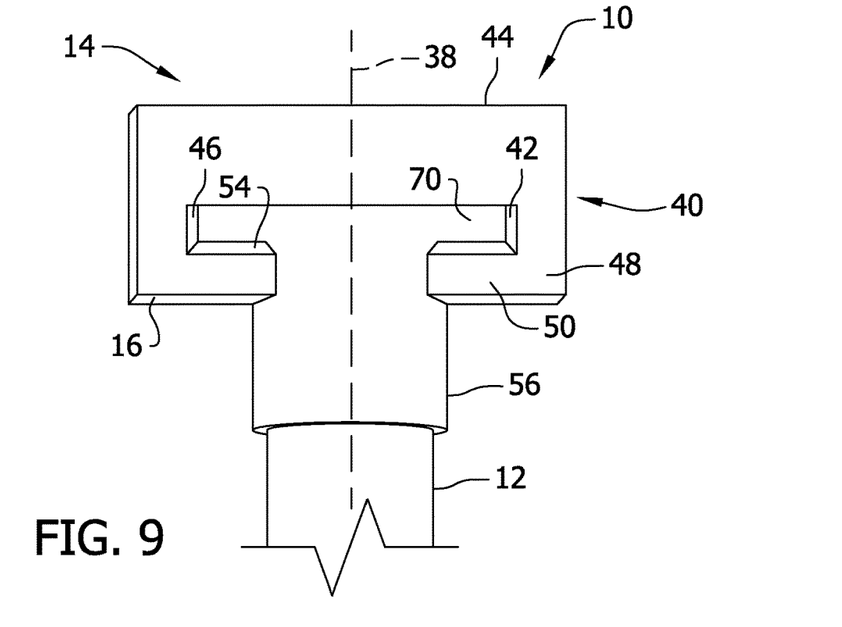
FIG. 9 is a partial view of the connector of FIG. 1 being fully inserted into the gastrostomy tube.

FIG. 8 shows the connector 10 being partially inserted into the gastrostomy tube 12 and FIG. 9 shows the connector 10 being fully inserted into the gastrostomy tube 12. The gastrostomy tube 12 was first slipped over the insertion tube 58, thereby engaging with the abutments 68. After reaching the connecting surface 46 the connector 10 was turned. The gastrostomy tube 12 comprises one or more wings 70 at the end portion 56 which are inserted into the receiving recess 42. According to FIGS. 8 and 9 the end portion 56 is formed as an adaptor disposed at the end of the gastrostomy tube 12. The adaptor can be a separate member slipped over the end of the gastrostomy tube 12. Alternatively, it is possible that the end portion of the gastrostomy tube 12 is adapted to have the wings 70. In both cases the connector 10 and the gastrostomy tube 12 are securely and closely connected to each other. The secured locking of the gastrostomy tube 12 and the connector 10 is achieved by the insertion tube 58 being inserted into the gastrostomy tube 12 and the wings 70 of the end portion 56 being inserted in the receiving recess 42 (or recesses) of the bayonet style locking member 16. Preferably, the insertion tube 58 is tapered (as explained below).

Figure 10:
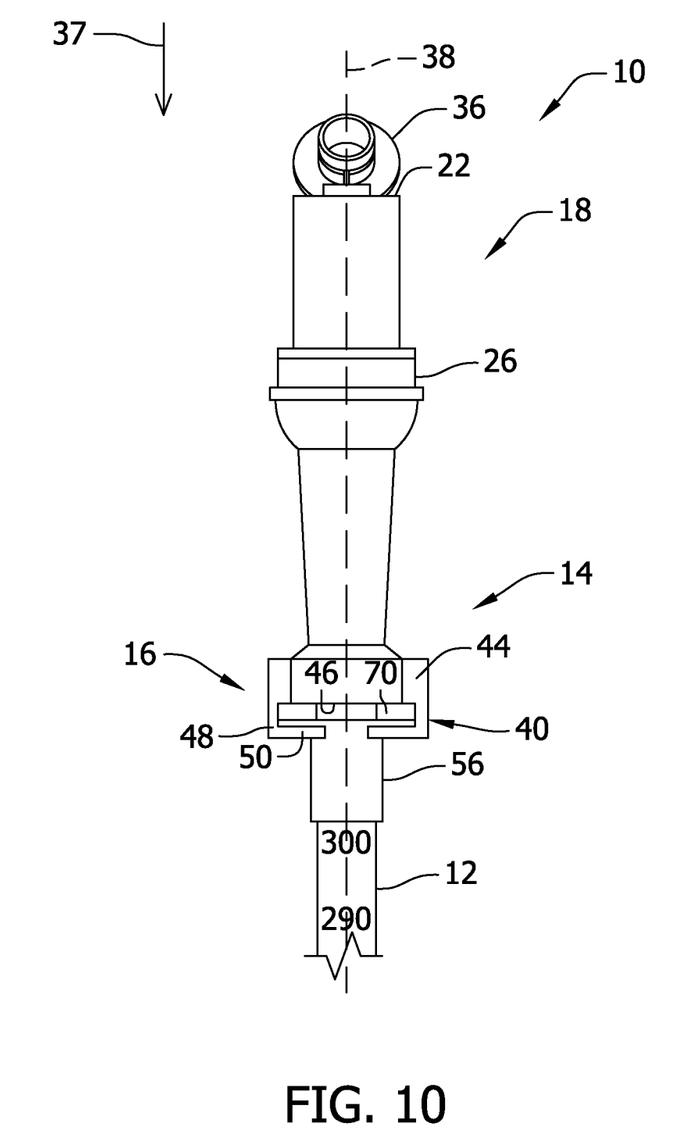
FIG. 10 is a front view of an assembly with the connector of FIG. 1 being connected to the gastrostomy tube.

FIG. 10 also shows a connector assembly comprising the connector 10 being fully connected with the gastrostomy tube 12. After connecting the gastrostomy tube 12 with the connector 10 a syringe (not shown) can be attached to the syringe attachment member 20. The FIGS. 8 to 10 relate to both embodiments, i.e. the first and the second embodiment.

The gastrostomy tube 12 is inserted into a stoma at a patient's body to allow nutritional formula to be delivered directly to the stomach. A Y-port connector 10 can be used in conjunction with a gastrostomy tube 12 to allow syringes (not shown) supplying medication or supplements to be attached to the gastrostomy tube 12. The Y-port connector 10 can be adapted to facilitate different syringes, such as luer-lock syringes or a catheter-slip syringe.

Thus, another aspect of the present invention relates to a Y-port connector 10 for use in conjunction with a gastrostomy tube 12 and more specifically to a Y-port connector 10 having a bayonet locking style system. A Y-port connector 10 having syringe ports (syringe attachment member 20) for attaching syringes to a gastrostomy tube 12 should be securely fastened to the gastrostomy tube 12. The Y-port connector 10 of the current invention can include a bayonet mount integrally formed or bonded at one end (first connector portion 14). The bayonet mount can be configured to receive lateral extending locking wings 70 at the top or end portion 56 of the gastrostomy tube 12. The bayonet mount can have sloped edges 54 for ease of inserting the locking wings 70 in the mount (receiving recess 42).

The insertion tube 58 can also be designed as a tapered stepped extension configured to be received in the gastrostomy tube 12 to securely attach the Y-port connector 10 to the gastrostomy tube 12. The stepped extension is inserted in the gastrostomy tube 12 first and then the locking wings 70 of the gastrostomy tube 12 are inserted in the bayonet mount (receiving recess 42).

Thus, connector 10 allows for syringes to be attached to the gastrostomy tube 12 to enable medication/supplements be given to the patients. The utilization of the bayonet style locking system can secure the connecting of connector 10 to gastrostomy tube 12.

The main difference between the two embodiments of the connector 10 shown in FIGS. 1 to 3 and 4 to 6, respectively is the luer adaptor which is fitted to the connector 10 of FIGS. 1 to 3. This is to facilitate connection of a luer locking syringe with the ability to connect an oral syringe to the side port. The design of the connector 10 shown in FIGS. 4 to 6 supports a luer- and catheter-slip syringe.

Listing of Reference Numbers

| | |
|---|---|
| 10 | connector |
| 12 | gastrostomy tube |
| 14 | first connector portion |
| 16 | bayonet style locking member |
| 18 | second connector portion |
| 20 | syringe attachment member |
| 22 | feeding attachment member |
| 24 | first arm |
| 26 | second arm |
| 28 | adaptor |
| 32 | Y-bridge |
| 34 | adaptor cap |
| 36 | feeding cap |

-continued

Listing of Reference Numbers

| | |
|---|---|
| 37 | longitudinal direction |
| 38 | longitudinal axis |
| 40 | locking projection |
| 42 | receiving recess |
| 44 | body portion |
| 46 | connecting surface |
| 48 | connecting portion |
| 50 | free end portion |
| 54 | edges |
| 56 | end portion |
| 58 | insertion tube |
| 60 | orifice |
| 62 | passing recess |
| 64 | tube portion |
| 66 | outer surface |
| 68 | abutment |
| 70 | wings |

The invention claimed is:

1. A connector for connecting a syringe to a gastrostomy tube, the connector comprising a bayonet style locking member with a locking projection for locking the connector to the gastrostomy tube and an insertion tube extending along a longitudinal axis of the connector, the insertion tube is configured to be received in the gastrostomy tube,
wherein the locking projection forms a receiving recess for receiving and locking at least one wing of an end portion of the gastrostomy tube,
wherein the bayonet style locking member further comprises a body portion with a connecting surface and with a through hole extending in a longitudinal direction along the longitudinal axis of the connector, and
wherein the locking projection comprises a connecting portion extending substantially in the longitudinal direction and a free end portion extending substantially perpendicular to the connecting portion toward the insertion tube, the insertion tube extending from a position proximal of the free end portion to a position distal of the free end portion along the longitudinal axis.

2. The connector according to claim 1, wherein the receiving recess is formed by at least one of the connecting portion, the free end portion and the connecting surface.

3. The connector according to claim 1, wherein the receiving recess extends in a linear shape or in an arc shape substantially perpendicular to the longitudinal direction.

4. The connector according to claim 1, wherein the free end portion comprises edges forming the receiving recess, the edges being inclined for narrowing the edges to the receiving recess.

5. The connector according to claim 1, further comprising at least two locking projections, the free end portions of the at least two locking projections pointing toward each other and being distanced to define an orifice in between.

6. The connector according to claim 5, wherein the insertion tube extends through the orifice.

7. The connector according to claim 1, wherein the insertion rube contacts the connecting surface and extends substantially in the longitudinal direction.

8. The connector according to claim 1, further comprising a passing recess between the free end portion and the insertion tube.

9. The connector according to claim 1, wherein the insertion tube comprises a plurality of tube portions, each tube portion tapered at an outer surface in the longitudinal direction for forming a plurality of abutments.

10. The connector according to claim 1, further comprising a first connector portion comprising the bayonet style locking member and a second connector portion comprising a syringe attachment member for attaching the syringe, the second connector portion being substantially Y-shaped or T-shaped with a first arm comprising the syringe attachment member and a second arm extending at an angle to the first arm and comprising a feeding attachment member for attaching a feeding tube or a container, each of the first and second arms defining respective fluid passages, a fluid passage of the second arm extending at an angle to a fluid passage of the first arm.

11. The connector according to claim 10, further comprising an adaptor attached to the first arm.

12. The connector according to claim 1, wherein the free end portion of the locking projection extends radially inward from the connecting portion such that the free end portion is configured to engage an outer surface of the gastrostomy tube when the insertion tube is inserted into the gastrostomy tube.

13. A connector assembly comprising the connector of claim 1 and an end portion of a gastrostomy tube being integrally formed with the gastrostomy tube or being formed as an adaptor, wherein the end portion comprises at least one wing configured to be received in the receiving recess.

14. A method of connecting a syringe to a gastrostomy tube, comprising:
   providing a connector according to claim 1;
   providing a gastrostomy tube with an end portion having at least one wing to be connected with the connector, the end portion being integrally formed with the gastrostomy tube or being formed as an adaptor;
   slipping the gastrostomy tube over an insertion tube of the connector;
   turning the connector to engage the wing of the gastrostomy tube with the receiving recess;
   providing a syringe; and
   attaching the syringe at a syringe attachment member of the connector.

15. The method according to claim 14, further comprising engaging an outer surface of the gastrostomy tube with the free end portion of the locking projection when the gastrostomy tube is slipped over the insertion tube.

16. A connector for connecting a syringe to a gastrostomy tube, the connector comprising a bayonet style locking member with a locking projection for locking the connector to the gastrostomy tube, and an insertion tube extending along a longitudinal axis of the connector, the insertion tube configured to be received in the gastrostomy tube,
   wherein the locking projection forms a receiving recess for receiving and locking at least one wing of an end portion of the gastrostomy tube,
   wherein the bayonet style locking member further comprises a body portion with a connecting surface and with a through hole extending in a longitudinal direction along the longitudinal axis of the connector, and
   wherein the locking projection comprises a connecting portion extending substantially in the longitudinal direction and a free end portion extending substantially perpendicular to the connecting portion,
   the connector further comprising a first connector portion comprising the bayonet style locking member and a second connector portion comprising a syringe attachment member for attaching the syringe, and the insertion tube extending from within the locking projection past the free end portion of the locking projection.

17. The connector according to claim 16 wherein the second connector portion is substantially Y-shaped or T-shaped with a first arm comprising the syringe attachment member and a second arm extending at an angle to the first arm and comprising a feeding attachment member for attaching a feeding tube or container, each of the first and second arms defining respective fluid passages, the fluid passage of the second arm extending at an angle to the fluid passage of the first arm.

18. The connector according to claim 17, wherein the free end portion of the locking projection extends radially inward from the connecting portion such that the free end portion is configured to engage an outer surface of the gastrostomy tube when the insertion tube is inserted into the gastrostomy tube.

19. The connector according to claim 17, further comprising an adaptor attached to the first arm.

20. A connector for connecting a syringe to a gastrostomy tube, the connector comprising:
   a bayonet style locking member with a locking projection for locking the connector to the gastrostomy tube; and
   an insertion tube extending along a longitudinal axis of the connector, the insertion tube configured to be received in the gastrostomy tube,
   the locking projection forming a receiving recess for receiving and locking at least one wing of an end portion of the gastrostomy tube, the bayonet style locking member further comprising a body portion with a connecting surface and with a through hole extending in a longitudinal direction along the longitudinal axis of the connector,
   the locking projection comprising a connecting portion extending substantially in the longitudinal direction and a free end portion formed integrally with the connecting portion and extending substantially perpendicular to the connecting portion and radially inwardly from the connecting portion toward the insertion tube.

\* \* \* \* \*